United States Patent [19]

Bron

[11] Patent Number: 4,998,556
[45] Date of Patent: Mar. 12, 1991

[54] DRIP EMITTER

[76] Inventor: Dan Bron, 36 Palmach St., Haifa, Israel

[21] Appl. No.: 280,971

[22] Filed: Dec. 7, 1988

Related U.S. Application Data

[63] Continuation-in-part of Ser. No. 21,494, Mar. 4, 1987, Pat. No. 4,796,660.

[30] Foreign Application Priority Data

Mar. 5, 1986 [IL] Israel .................................. 78045

[51] Int. Cl.⁵ .......................................... F16K 31/365
[52] U.S. Cl. ................................................. 137/501
[58] Field of Search ................. 137/501, 504, 505.37

[56] References Cited

U.S. PATENT DOCUMENTS

| | | | |
|---|---|---|---|
| 375,071 | 12/1887 | Jackson | 137/501 |
| 3,103,232 | 9/1963 | Ritter et al. | 137/505.37 |
| 4,343,305 | 8/1982 | Bron | 137/501 X |
| 4,513,777 | 4/1985 | Wright | 137/504 X |

FOREIGN PATENT DOCUMENTS

| | | | |
|---|---|---|---|
| 896214 | 2/1945 | France | 137/501 |
| 1062438 | 4/1954 | France | 137/501 |
| 3134 | of 1887 | United Kingdom | 137/501 |

Primary Examiner—Stephen M. Hepperle

[57] ABSTRACT

An improvement of an adjustable-rate, flow-regulated, constant-output emitter comprising a flow-regulating valve having a valve head accessible to the high-pressure liquid and a valve stem one end of which is attached to, or integral with, the valve head, and a valve seat associated with the valve head and located in a high-pressure region upstream of a first chamber, the valve seat and the valve head defining between them a gap through which the liquid passes on its way from the high-pressure source into the first chamber, wherein the valve head is adapted to be acted upon by a first force tending to reduce the gap, and by a second force tending to increase the gap, a state of equilibrium between the forces defining the set point of the flow-regulated emitter.

4 Claims, 2 Drawing Sheets

DRIP EMITTER

This application is a continuation-in-part of a prior copending U.S. Pat. application Ser. No. 021,494 filed in the U.S. Patent Office on Mar. 4, 1987, Pat. No. 4,796,660.

The present invention relates to an adjustable-rate, constant output emitter, that is, to an emitter adjustable to a wide range of flow or dripping rates and, once adjusted to a certain rate, maintains that rate throughout the entire emission period.

Although at least some of the examples described hereinbelow are explained with reference to a special type of emitter, namely an infusion set, it should be understood that the features claimed are appropriate also to emitters for other purposes, e.g., drip-irrigation emitters and the like.

Infusion, or more precisely, intravenous infusion is today a standard procedure both as emergency treatment for loss of blood, shock, dehydration, etc., and as therapeutic routine in a great many conditions also requiring the slow infusion of various liquids other than whole blood, plasma and saline. Whatever liquid is used, is gravity-fed into the patient's venous system over periods of time that may extend over hours and even days.

Of particular importance for the efficacy of the infusion treatment is a steady dripping rate, yet it is precisely in this point that the standard infusion set fails: within the first two hours, there is a dripping-rate falloff of almost 25%. While this is to a great extend due to the flow-control clamp, there are also other causes such as variations of the fluid level in the container with respect to the position of the patient, variations in the venous pressure of the latter, and partial clogging of the hypodermic needle or cannula used. This obliges the medical staff to spend additional time monitoring and readjusting the infusion set, and even so, the use of the standard infusion set is liable to result in a non-uniform and sometimes improper dripping rate.

While these disadvantages were largely overcome by the recently developed flow-regulated, constant-output infusion sets, for instance the infusion set disclosed in U.S. Pat. No. 4.343,305, experience has shown that the many advantages of the constant-output, flow-regulated infusion set are at least partly offset by the fact that, regulation taking place at the low-pressure outlet opening, the infusion set is liable to act as a "dirt trap", filtering out all the solid impurities from the infusion fluid (blood clots, undissolved medications, precipitates, etc.) and rapidly becoming clogged. In spite of the various improvements introduced in recent years with the aim of remedying this situation, the fact remains that as far as the ability to resist clogging is concerned, the flow-regulated infusion set has so far been greatly inferior to the conventional, non-regulated set.

It is one of the objects of the present invention to overcome the disadvantages of prior-art flow-regulated infusion sets, and to provide a flow-regulated infusion set that, while retaining the well-known advantages of these infusion sets, is largely non-clogging.

According to the invention, this is achieved by providing in an adjustable-rate, flow-regulated, constant-output emitter comprising: an inverted-cup-shaped connector piece connectable to a source of relatively high-pressure liquid and having substantially cylindrical walls and a downward-facing bottom surface provided with an inlet port, a head piece rotatably engaging said connector piece: an intermediate member having an outlet port, said member being interposed between, and rotatable relative to either of, said connector piece and said head piece, an elastically deformable diaphragm at least the radial position of which is maintained by said member and which diaphragm defines with its upper surface a first chamber comprising said inlet port, and with its lower surface a second chamber comprising said outlet port; passageway means leading from said first chamber via said member into said second chamber, said passageway means including at least one first portion in which flow is relatively unobstructed as well as at least one second portion in which flow is relatively restricted, the restrictive effect of which second portion determines the flow rate of said emitter, which restrictive effect can be varied by means of a rotary displacement of one of said pieces relative to the other, an improvement comprising: a flow-regulating valve comprised of a valve head accessible to said high-pressure liquid and a valve stem one end of which is attached to, or integral with, said valve head, and a valve seat associated with said valve head and located in a high-pressure region upstream of said first chamber, said valve seat and said valve head defining between them a gap through which the liquid passes on its way from said high-pressure source into said first chamber, wherein said valve head is adapted to be acted upon by a first force tending to reduce said gap, and by a second force tending to increase said gap, a state of equilibrium between said forces defining the set point of said flow-regulated emitter.

The invention will now be described in connection with certain preferred embodiments with reference to the following illustrative figures so that it may be more fully understood.

With specific reference now to the figures in detail, it is stressed that the particulars shown are by way of example and for purposes of illustrative discussion of the preferred embodiments of the present invention only and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Figure 1:
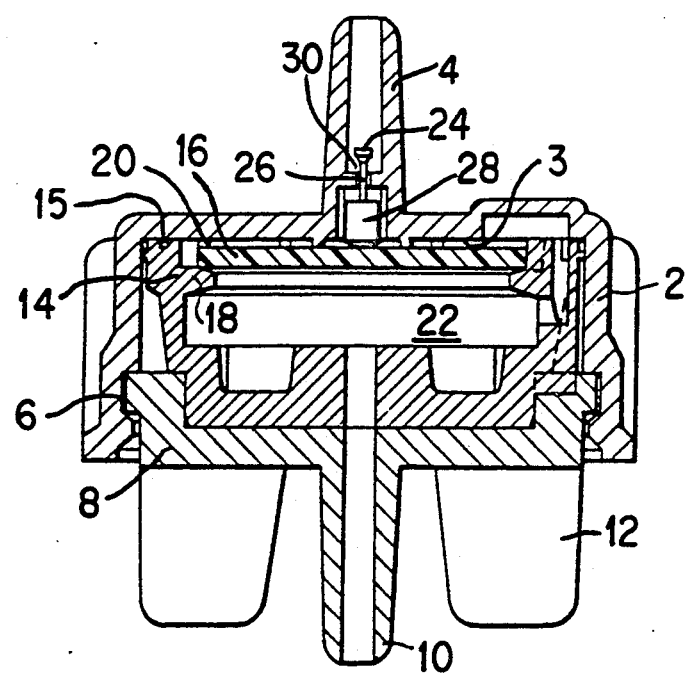
FIG. 1 is a cross-sectional view of a first embodiment of the emitter according to the invention, with the valve-stem terminal freely resting on the diaphragm.

Referring now to the drawings, there is seen in FIG. 1 a connector piece 2 in the form of an inverted cup with substantially cylindrical walls, a downward-facing bottom surface 3 and an inlet connector 4 opening into the bottom surface and connectable to a source of relatively high-pressure liquid which, if this embodiment is used as a drip-irrigation emitter, is usually a supply pipe and, when used as an "in-line" infusion set, is a vessel containing the infusion liquid.

Rotatably engaging the connecting piece 2 via. e.g., a snap joint 6, there is seen a head piece 8 including an outlet connector 10 and two wing-like projections 12 by means of which, for a purpose to be explained further below, the connecting piece 2 and the head piece 8 can be rotated relative to one another.

Inside the housing formed by the assembled connector piece 2 and the head piece 8 there is seated an intermediate member 14 of a cup-like shape extending from the bottom of a recess in the head piece 8 to the bottom surface 3 of the connecting piece 2. Radial recesses (not shown) in the rim of the head piece 8 and matching lugs (not shown) immobolize the intermediate member 14 relative to the head piece 8, in other words, these two components cannot rotate independently of each other.

An arcuate groove 15 is provided in the rim like upper surface of the intermediate member 14. This groove is clearly shown in several views under numeral 42 in FIGS. 6.7 and 8 of the aforementioned U.S. Pat. No. 4,343,305 and constitutes the flow-restrictive element on which is based the adjustable-rate feature of the device according to the invention. The shape of this element as well as the manner in which it functions are explained in detail in the above U.S. disclosure (col. 4, lines 33–68, col. 5, lines 1–23) and need not be gone into here. 4, lines An elastically deformable diaphragm 16 is freely supported on a ledge-like annular projection 18 and divides the housing into a first, inlet, chamber 20 and a second, outlet, chamber 22.

There is further provided a valve assembly comprised of a conical valve head 24, carried by a valve stem 26, to the free end of which is attached a terminal piece 28 freely resting on the diaphragm 16. The annular edge of the bore through which the valve stem 26 passes with clearance serves as valve seat 30 to the valve head 24. The above edge is advantageously provided with a narrow chamfer. The valve head, as is obvious from FIG. 1, is always accessible to the already mentioned high-pressure liquid.

FIG. 1 shows the emitter in the empty state, in which the valve head 24, supported by the—at this stage—substantially flat diaphragm 16, is lifted clear off the valve seat 30. When now the liquid supply is connected, liquid at the relatively high supply-line pressure starts to flow via the inlet connector 4 through the annular gap between valve head 24 and valve seat 30 first into the inlet chamber 20 and then, via the flow-restricting groove 15, into the outlet chamber 22. The resistance offered by the groove 15 produces a perceptible pressure drop between the inlet and outlet chamber. This pressure drop or differential pressure causes the diaphragm 16 to bulge downward (by elastically flexing), thereby also permitting the valve assembly (terminal 28, stem 26 and head 24) to drop relative to the emitter housing. As a consequence of this, the valve head 24 approaches the valve seat 30, the above-mentioned gap is reduced and inflow into the inlet chamber 20 is progressively diminished. Since at the same time outflow through the outlet socket 10 continues, pressure in the inlet chamber 20 drops, and the differential pressure, i.e., the difference between the pressures in the two chambers 20 and 22, drops too. This enables the natural elasticity of the diaphragm 16 to reduce the bulge produced by the previously high differential pressure. Now, a reduction of the bulge, that is, a flattening of the diaphragm will obviously cause the valve assembly to be raised, thereby again enlarging the gap between valve head 24 and valve seat 30, and thus increase inflow, starting the above-described cycle again. A state of equilibrium is eventually achieved, when the bulging force, i.e., the differential pressure, and the restoring force, i.e., the resilience of the diaphragm, become substantially equal. This state defines the so-called set point of this flow-regulating system which makes emitter output largely independent of line pressure and its fluctuations.

In actual operation of the emitter according to the invention, the gap slightly oscillates about a width of less than 0.1 mm, which explains the filtering effect of the emitters according to the invention: solid particles of a size that in prior-art flow-regulated emitters will cause clogging, are simply not admitted by the 0.1 mm-gap. Particles smaller than 0.1 mm will harmlessly pass through the flow-restricting groove 15.

Figure 2:
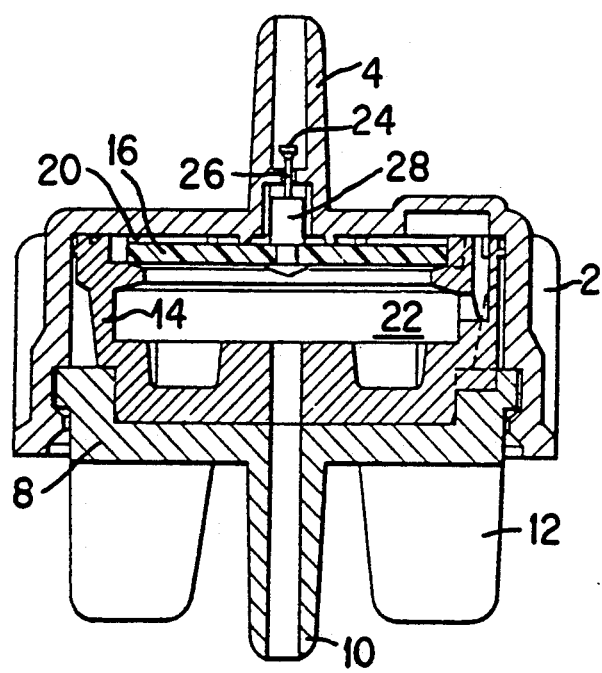
FIG. 2 shows a similar view of a second embodiment of the emitter, in which the valve stem is fixedly connected to the diaphragm via the valve-stem terminal.

FIG. 2 illustrates an emitter that is similar to that shown in FIG. 1, except for the valve-stem terminal 28 which in this embodiment is fixedly attached, for example by riveting, to the diaphragm 16.

Figure 3:
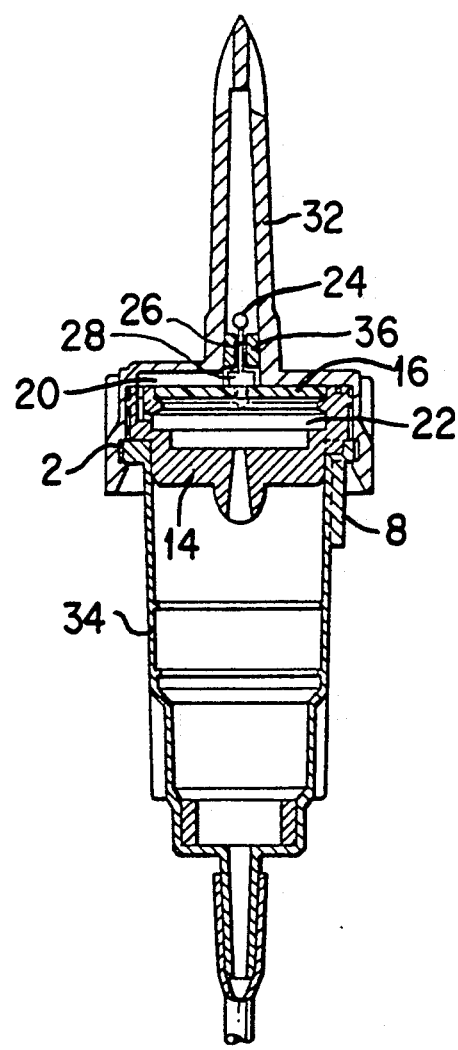
FIG. 3 is a cross-sectional view of a third embodiment, including a drip chamber.

In FIG. 3 the emitter according to the invention is in the form of the infusion set of the abovementioned U.S. disclosure, being now provided with a snout 32 for introduction into the infusion-liquid bag, and with a transparent drip chamber 34. An inlet sleeve 36 is seen to have been introduced into the lower portion of the snout 32 to constitute the valve seat 30 (Fig. 1) and to accomodate the valve assembly. In this embodiment, the valve head 24 is seen to be spherical.

It will be evident to those skilled in the art that the invention is not limited to the details of the foregoing illustrative embodiments and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. In an adjustable-rate, flow regulated, constant-output emitter comprising:

an inverted-cup-shaped connector piece connectable to a source of relatively high-pressure liquid and having substantially cylindrical walls and a downward-facing bottom surface provided with an inlet port, a head piece rotatably engaging said connector piece;

an intermediate member having an outlet port, said member being interposed between, and rotatable relative to either of, said connector piece and said head piece, an elastically deformable diaphragm at least the radial position of which is maintained by small member and which diaphragm defines with its upper surface a first chamber comprising said inlet port, and with its lower surface a second chamber comprising said outlet port;

passageway means leading from said first chamber via said member into said second chamber, said passageway means including at least one first portion in which flow is relatively unobstructed as well as at least one second portion in which flow is relatively restricted, the restrictive effect of which second portion determines the flow rate of said emitter, which restrictive effect can be varied by means of a rotary displacement of one of said pieces relative to the other, an improvement comprising:

a flow-regulating valve comprised of a valve head accessible to said high-pressure liquid and a valve stem one end of which is attached to, or integral with, said valve head, and a valve seat associated with said valve head and located in a high-pressure region upstream of said first chamber, said valve seat and said valve head defining between them a gap through which the liquid passes on its way from said high-pressure source into said first chamber, wherein said valve head is adapted to be acted upon by a first force tending to reduce said gap, and by a second force tending to increase said gap, a state of equilibrium between said forces defining the set point of said flow-regulated emitter, wherein during operation, the maximum opening size of said gap defined by said valve head and said valve seat is smaller then the maximum opening provided by the flow-restrictive portion of said flow-restrictive passageway.

2. The emitter is claimed in claim 1, wherein the free end of said valve-stem terminal freely rests on said diaphragm.

3. The emitter as claimed in claim 1, wherein the end of said valve-stem terminal is fixedly attached to said diaphragm.

4. The emitter as claimed in claim 1, wherein said first force is produced by a pressure difference between said first chamber and said second chamber, and said second force is produced by the natural elasticity of said diaphragm.

* * * * *